United States Patent
Basagañas Millan

(10) Patent No.: US 6,374,045 B2
(45) Date of Patent: Apr. 16, 2002

(54) MULTI-USE HEATING DEVICE FOR VAPORIZING ACTIVE SUBSTANCES

(75) Inventor: Jordi Basagañas Millan, Barcelona (ES)

(73) Assignee: DBK España, S.A., Barcelona (ES)

( * ) Notice: Subject to any disclaimer, the term of this patent is extended or adjusted under 35 U.S.C. 154(b) by 0 days.

(21) Appl. No.: 09/770,591

(22) Filed: Jan. 26, 2001

Related U.S. Application Data

(63) Continuation of application No. PCT/ES99/00240, filed on Jul. 28, 1999.

(30) Foreign Application Priority Data

Jul. 28, 1998 (ES) ................................................ 9801592

(51) Int. Cl.⁷ .................................................. F24F 6/08
(52) U.S. Cl. ...................................... 392/395; 392/391
(58) Field of Search ................................. 392/386, 390, 392/391, 392, 394, 395; 122/366; 261/139, 140.2, 142, 99

(56) References Cited

U.S. PATENT DOCUMENTS

| | | | | |
|---|---|---|---|---|
| 4,728,779 A | * | 3/1988 | Kotani et al. ................ | 219/540 |
| 4,874,924 A | * | 10/1989 | Yamamoto et al. .......... | 392/395 |
| 5,222,186 A | * | 6/1993 | Schimanski et al. ......... | 392/395 |
| 5,574,821 A | * | 11/1996 | Babasade ..................... | 392/392 |
| 5,940,577 A | * | 8/1999 | Steinel ......................... | 392/395 |
| 6,148,143 A | * | 11/2000 | Steinel, Jr. ................... | 392/390 |

FOREIGN PATENT DOCUMENTS

| | | | |
|---|---|---|---|
| DE | 19806269 | * | 2/1999 |
| FR | 2054435 | * | 7/1993 |

* cited by examiner

Primary Examiner—Sang Paik
(74) Attorney, Agent, or Firm—Rosenman & Colin LLP

(57) ABSTRACT

A housing within which a resistor is arranged is connected to two connections projecting through the bottom of the housing. The housing is further provided with an aluminum plate serving as a radiator which is held inside at the top of the housing, held by strips in the latter. The housing and the aluminum plate are provided with a hole through which a wick may pass to project through the mouth of a container holding liquid product to be vaporized by heating the wick through the resistor. A frame-like spacer element is arranged on the housing and fixed thereto, defining a supporting surface for a tablet, which tablet may be spaced to a greater or lesser extent by the spacer element in order for said tablet to be reached at all times by the appropriate heat to be full efficiently vaporized.

3 Claims, 3 Drawing Sheets

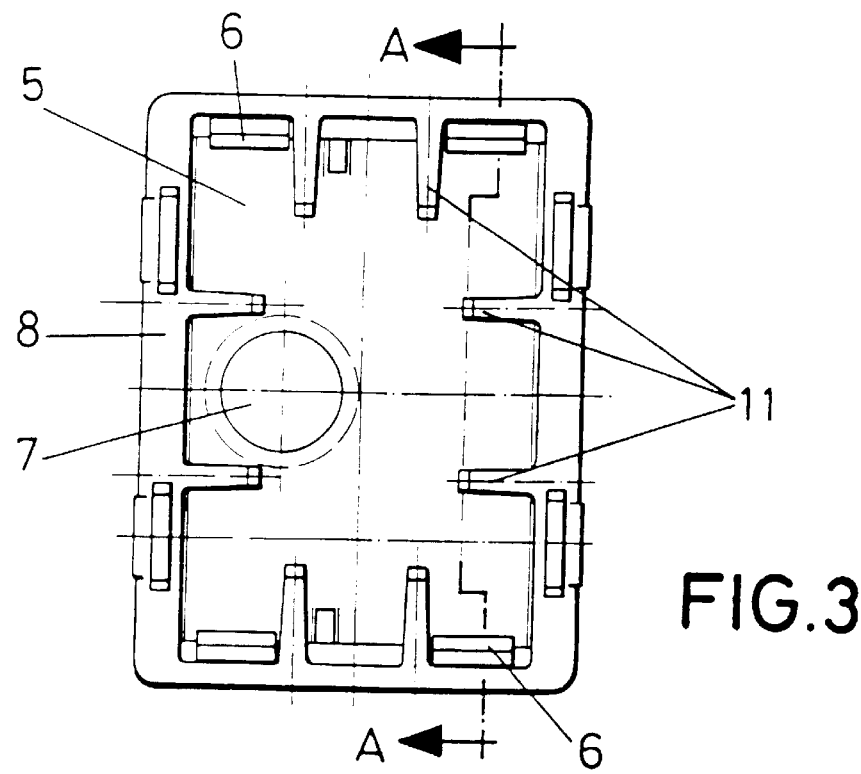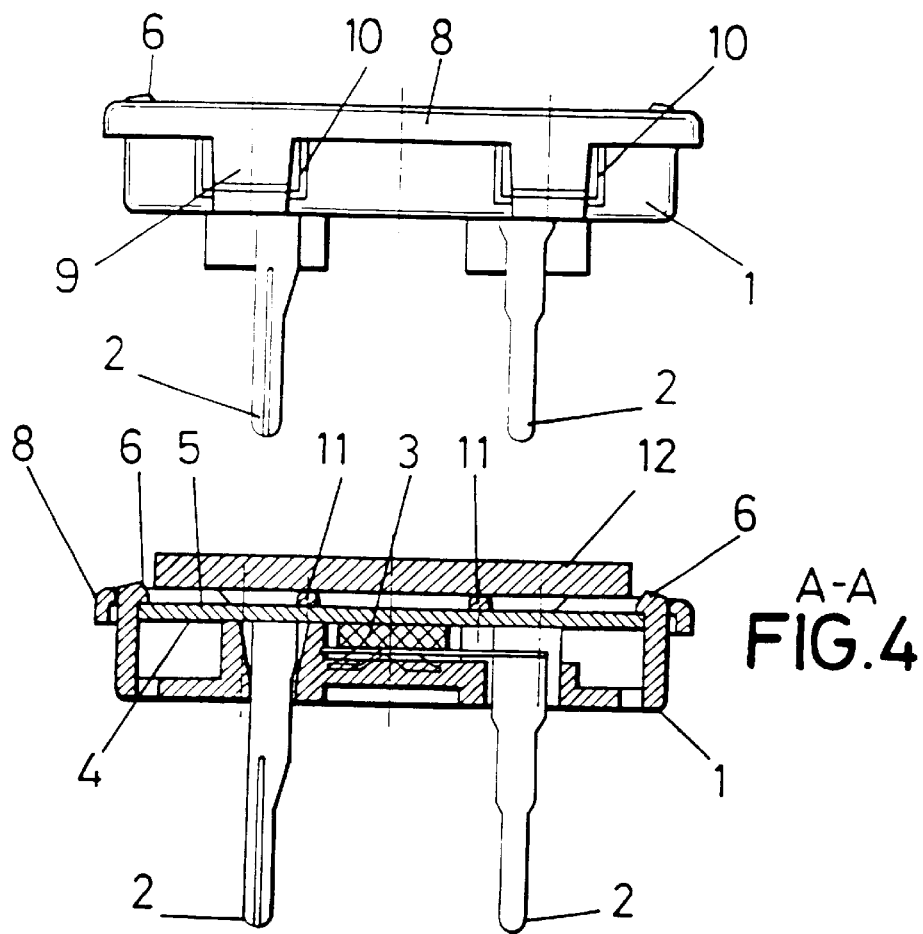

MULTI-USE HEATING DEVICE FOR VAPORIZING ACTIVE SUBSTANCES

This is a continuation of PCT application Ser. No. PCT/ES99/00240 filed on Jul. 28, 1999.

OBJECT OF THE INVENTION

The invention relates to a multipurpose heating device designed to stand as a means for vaporising active substances, such as those used as insecticides or air-fresheners. The device, which is provided with a resistor, preferably of the PTC type, as the heating means, is structured to be able to evaporate liquids, tablets and gels without distinction, and at all times with a maximum performance, whatever the type of product to be evaporated may be.

BACKGROUND OF THE INVENTION

There are electrically powered heating devices for vaporising liquids contained in diffusers, in some cases, and solids in the form of tablets in other cases, and indeed sometimes allowing tablets or liquids to be used without distinction, at will.

Present-day known devices for vaporising these products usually consist of a resistor which upon being activated heats a ceramic plate through which the relevant substance is vaporised close to a tablet diffuser. On the other hand, the heating device may be provided with a hole in which a wick is arranged projecting to the outside of a diffuser container holding a liquid product, thereby for heating of that wick to cause the liquid substance held in the container to be vaporised.

The power required in heating the heating device differs in the case of diffusers containing liquids and solid or tablet products, because in the first case a greater temperature is required at the mouth of the hole, whereas in the latter case the entire surface of the tablet can come into contact with the ceramic plate, whence less heat is required for sublimation to take place.

That is why a same heating device is neither advisable nor indeed effective to be able to vaporise tablet form products and vaporise liquid products without distinction, because the optimum working temperature of the wick in the case of liquid products does not match that of the tablet in the case of solid products, and therefore two types of heating devices are normally marketed, one specific for liquids and another one which is also specific for solids or tablets.

DESCRIPTION OF THE INVENTION

The heating device disclosed herein has been devised to fully overcome the above-mentioned drawbacks, i.e. it may be used without distinction and as may be required on case by case basis for liquid products or for tablet form products.

More specifically, the first novel characteristic of the heating device subject of the invention lies in that the general body of the heating device is supplemented with a spacer element provided with fixing means to the general body of the heating device, and therefore such spacer element may in each case be arranged at a greater or lesser distance from the heat radiating plate, thus allowing the solid product to be spaced to a greater or lesser extent; i.e. said spacer element is used to adjust the spacing between the tablet and the radiating plate in order to achieve an effective operation, starting from the fact that the heating device has previously been studied and constructed with a specific extent of evaporation and temperature to work as a heating device for liquid products, i.e. to work with a wick, and therefore taking that as the starting point, when the heating device is to be used to vaporise solid products, such as tablets, the spacer element will be used to adjust the spacing between the tablet and the radiating plate.

Another novel characteristic lies in that the heating plate at issue is not made of ceramics as is conventionally the case but consists of an aluminium plate. for an enhanced distribution of the temperature on the heater surface. and with that improvement the highest temperature reached on the surface of the aluminium radiating plate is less than in a ceramic heating device, thereby producing a lesser degradation of the insecticide active principles and of perfumes, due to an excess temperature, or in other words a better efficiency is achieved.

Another advantage of the inventive device lies in the perfect adjustment of the temperature required for each application, whether for liquid products or for tablets, based upon the above-mentioned spacer element.

DESCRIPTION OF THE DRAWINGS

In order to provide a fuller description and contribute to the complete understanding of the characteristics of the invention, in accordance with a preferred practical embodiment thereof, a set of drawings is attached to the specification as an integral part thereof which, while purely illustrative and not fully comprehensive, shows the following:

FIG. 3. Is a top plan view of the same heating device shown in the preceding figures, with the spacer element on which the relevant plate acting as an aluminium radiator is to be supported.

FIG. 4. Is a sectional view along line A—A of the preceding figure, with a tablet arranged supported on the spacer element.

PREFERRED EMBODIMENT OF THE INVENTION

Figure 1:
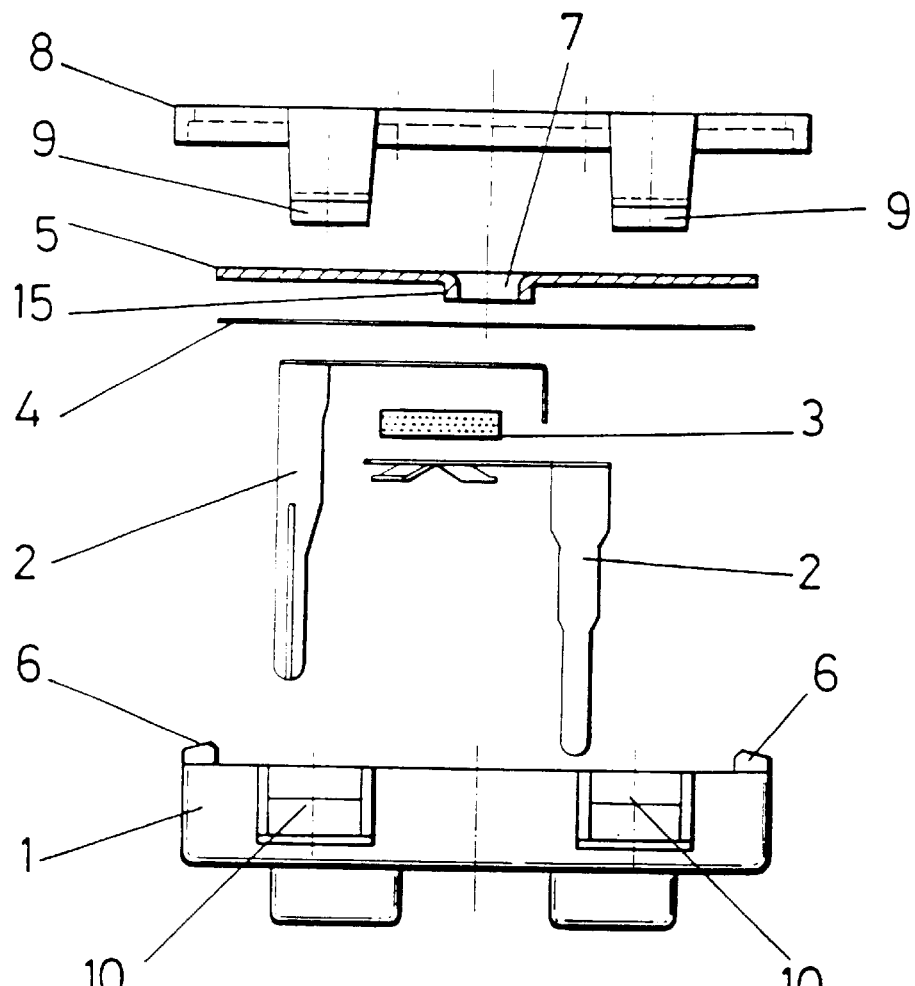
FIG. 1. Is an elevation exploded view of the various components making up the multipurpose heating device subject of the invention, showing a sectional view of the sheet or plate making up the aluminium radiator.
Figure 2:
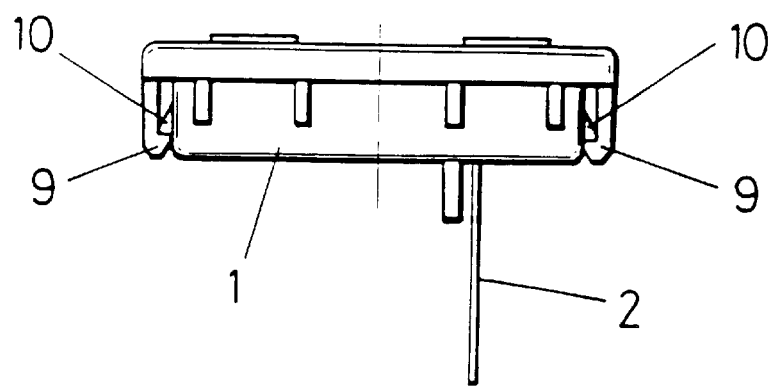
FIG. 2. Is a side elevation view of the fully mounted heating device.
Figure 5:
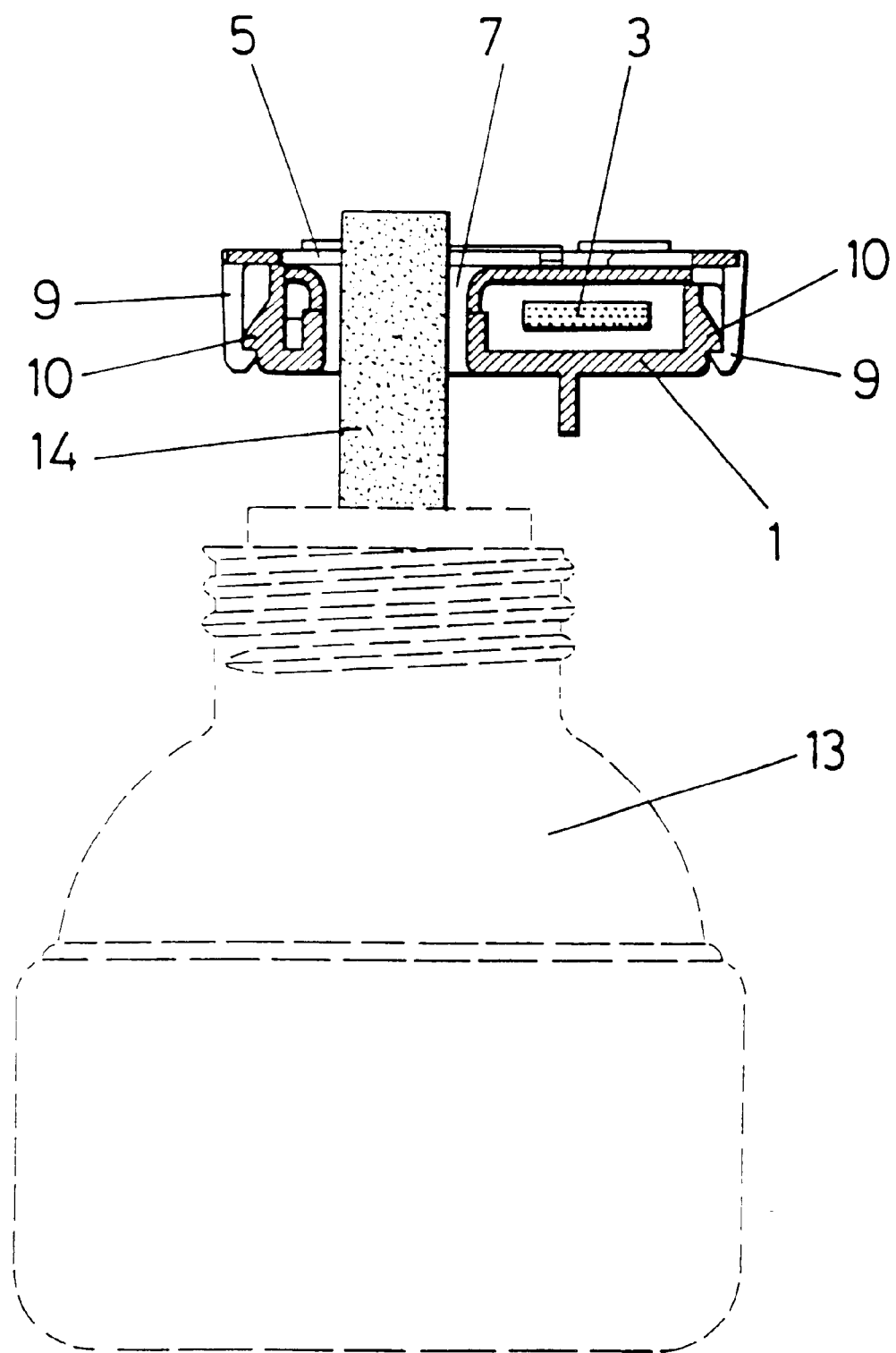
FIG. 5. Is another sectional view of the same heating device, as applied on a liquid diffuser container, with a wick projecting to the outside through which the relevant vaporisation takes place.

With reference to the above-mentioned figures, the heating device of the invention comprises a housing (1) with appropriate connections (2) passing through its base and a resistor (3) arranged between these, which connections (2) pass through appropriate windows or slots purposely provided on the base of the housing (1).

The resistor (3) is a PTC type resistor and has an isolating film (4) arranged above it, which lies just below the appropriate radiator (5), which in this case consists of an aluminium plate or sheet, the latter being held at the top of the housing (1) by means of elastic strips (6) with which said housing (1) is purposely provided on the top edges of two of its side-walls.

Both the housing (1) and the aluminium plate (5) constituting the radiator are provided with a hole (7).

The heating device thus constructed is further provided, and there lies one of the main characteristics of the invention, with a spacer element (8) consisting of a sort of frame coupled on the top contour of that device, and having side strips (9) or any other conventional means to be fixed by being locked onto appropriate steps (10) purposely provided on the respective faces of the housing (1).

This frame-like spacer element (8) has small projections (11) projecting inward from its sides, altogether forming a support for a tablet (12), as is clearly shown in FIG. 4.

In this way, and when the heating device is applied to vaporise a liquid product held in a container (13) from which a wick (14) emerges, passing through the hole (7) of the device, heat is conveyed through the bore or said hole (7) of the aluminium radiator (5), said heat being conveyed to the wick (14) with the assistance of the ledge (14), the latter increasing the heat radiation surface to the wick, causing the liquid held in the container (13) to be volatised or evaporated.

Clearly, and as aforesaid, the temperature supplied by the heating device will be adjusted to whatever is required for obtaining the desired evaporation speed.

If a solid product, in the form of both an insecticide and an air-freshener tablet (12), is to be evaporated, once the temperature required for the preceding case is fixed, the size of the spacer element (8) shall be adjusted in order to achieve a suitable spacing between said tablet (12) and the aluminium radiator (5) in order thereby to obtain a proper evaporation.

In conclusion, depending on the substances (insecticides, air-fresheners, etc.) or products to be evaporated (liquid, tablets, gels, etc.) the height of the spacer or separating element (8) shall be adjusted in each case, to achieve at all times a perfect adjustment for each case.

What is claimed is:

1. A multipurpose heating device for vaporising active substances, comprising:

a housing having a side surface, a base and a top, said top having an inner part, a resistor arranged in said housing and connected to said housing by at least one connecting element projecting through the housing base, a radiating element having a hole and fixed to said inner part of said housing top with strips, and a spacer fitted with fixing means to said housing, which spacer is furnished with means to support a tablet to be vaporised and maintain said tablet distanced from the radiating element, said spacer being the width of the support and distancing means, between the tablet and the radiating element, calculated previously so as to provoke a greater or lesser distance and with that, a greater or lower calorific contribution to the tablet.

2. A multipurpose heating device for vaporising active substances, as in claim 1, wherein the spacer for adjusting the spacing between the radiating plate and the tablet further comprises elastic strips locked in steps on the side surface of the housing said strips defining the fixing means of said spacer.

3. A multipurpose heating device for vaporising active substances, as in claim 1, wherein the radiating element further comprises an aluminum plate having a ledge around the hole to improve liquid evaporation.

* * * * *